United States Patent [19]
Rogers et al.

[11] Patent Number: 5,563,848
[45] Date of Patent: Oct. 8, 1996

[54] OBJECT DETECTOR FOR DETECTING BURIED OBJECTS

[75] Inventors: Andrew J. Rogers, Bentleigh; Charles G. Don, Murrumbeena, both of Australia

[73] Assignee: Monash University, Clayton, Australia

[21] Appl. No.: 302,279

[22] Filed: Sep. 8, 1994

[51] Int. Cl.⁶ .......................... G01S 15/04; G01N 29/00
[52] U.S. Cl. .................. 367/99; 367/13; 181/108; 73/594; 73/602
[58] Field of Search .................. 367/13, 87, 93, 367/99, 100, 101, 104, 37, 14; 73/584, 595, 598, 602; 181/108

[56] References Cited

U.S. PATENT DOCUMENTS

| | | | |
|---|---|---|---|
| 3,500,301 | 3/1970 | Meier | 367/13 |
| 4,128,011 | 12/1978 | Savage | 73/579 |
| 4,429,575 | 2/1984 | Akishaka | 73/598 |
| 4,922,467 | 5/1990 | Caulfield | 367/87 |
| 5,357,063 | 10/1994 | House et al. | 181/108 |

*Primary Examiner*—Ian J. Lobo
*Attorney, Agent, or Firm*—Needle & Rosenberg, P.C.

[57] ABSTRACT

An object detector for detecting metallic or non-metallic objects is disclosed which comprises a sound source such as a speaker (12) for generating impulse short sound bursts. A tube (16) conducts the acoustic signal from the speaker to the ground and at least one microphone M1–M3 is utilised for detecting reflections from the ground. A reflection from a buried object is compared with a reference signal which may be obtained from another microphone M1, M2 or earlier in time from the same microphone M3. The reflected and reference signals are subtracted to provide a difference signal and a difference signal is correlated with the original acoustic signal to provide an indication of an object. Time windows may be set to enable analysis of different depths to be obtained.

2 Claims, 6 Drawing Sheets

OBJECT DETECTOR FOR DETECTING BURIED OBJECTS

This invention relates to an object detector for detecting buried objects and in particular to a detector for detecting non-metal objects. The invention has particular application to the detection of non-metallic land mines.

Metal detectors for detecting buried metal objects are well known and can successfully detect such objects with a reasonably high degree of accuracy. However, such detectors obviously do not have any utility in detecting non-metallic objects such as objects made from plastics material.

The object of this invention is to provide a detector for detecting non-metallic objects.

The present invention provides an object detector for detecting objects buried in the ground, including:

a source for producing an acoustic signal and for directing the signal towards the ground so that the acoustic signal penetrates the ground;

a sensor for detecting a reflected signal from the object; and processing means for comparing the reflected signal with a reference signal indicative of a signal reflected from the ground, other than from where the object is buried, to thereby provide, based on said comparison, an indication of said object.

The present invention also provides an object detector for detecting objects buried in the ground, including:

a source for producing an acoustic signal and for directing the acoustic signal towards the ground so that the acoustic signal penetrates the ground;

a single sensor for, when the object detector is passed over the ground, detecting a reflected signal from the ground other than where the object is buried to thereby provide a reference signal and for detecting a reflected signal from the object;

a storage means for storing data relating to the reference signal; and processing means for comparing the reflected signal with the reference signal to thereby provide, based on said comparison, an indication of said object. Since the present invention relies on an acoustic signal and detecting a reflected signal from the object, the object can be detected regardless of the material from which it is made. Thus, the invention has application in detecting non-metallic objects as well as metallic objects.

In one preferred embodiment of the invention, the processing means compares the reference signal and reflected signal by subtracting the reference signal from the reflected signal to provide a difference signal. In this embodiment of the invention, the processing means also correlates the difference signal with the acoustic signal to compensate for random surface noise in the reference signal to obtain a modified difference signal x(t)

$$x(t) = \frac{\sum_{n=0}^{\infty} g(t) * s(t+n)}{[g(t)]^2}$$

wherein g(t) is the shape of the acoustic signal and s(t) is the reflected signal.

Preferably the acoustic signal is a short duration sound which is repeatedly produced by the source as the object detector is moved over the ground.

Preferred embodiments of the invention will be described, by way of example, with reference to the accompanying drawings in which.

The preferred embodiments of the invention to be described with reference to FIGS. 1 and 2 can be in the form of a detector which is similar to a metal detector which is intended to be held by a user and waved over the ground to be searched. Alternatively, the detectors can be truck mounted on the front of a truck with the control and processing componentry arranged in the rear of a truck. The latter embodiment has particular applications for sweeping ground to locate land mines and in such embodiments, a plurality of detectors or an array of detectors may be mounted on the front of a truck with a view to sweeping the entire width of a road or other terrain to be traversed by the truck as the truck moves over the ground.

Figure 1:
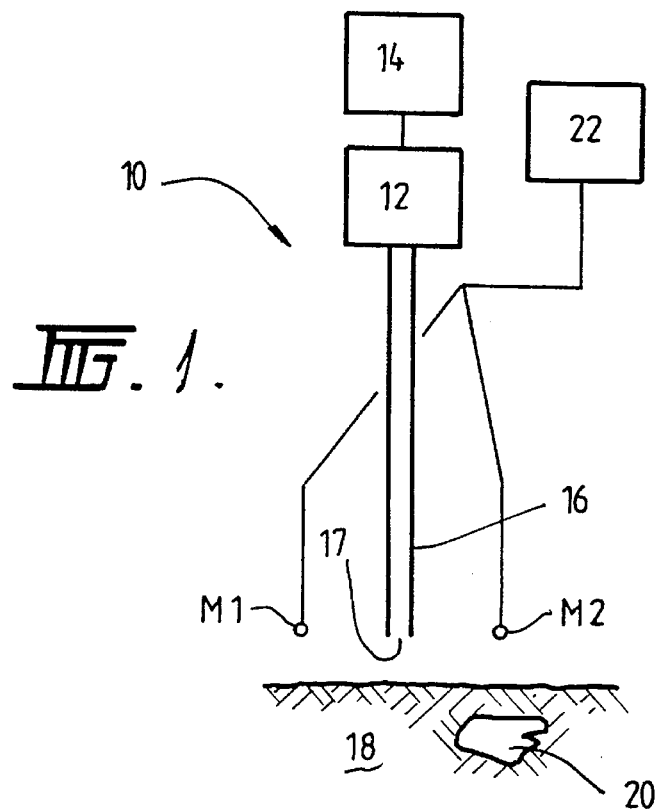
FIG. 1 is a schematic view showing a first embodiment of the invention.

With reference to FIG. 1, a detector 10 is shown which comprises a sound source such as a speaker or detonation means 12 for producing an impulse sound burst of relatively short duration. The sound bursts are continuously reproduced as the detector is passed over the ground. In the preferred embodiment of the invention where the source comprises a speaker, an amplifier and waveform synthesiser 14 is coupled to the speaker for powering the speaker to cause the speaker to reproduce the short duration sound bursts. The frequency of the acoustic signal is preferably in the audible spectrum and in the range 0 to 20 KHz.

The speaker 12 is coupled to a tube 16 of length approximately 1 meter so that the acoustic sound signals produced by the speaker or the detonation means travel down the tube 16 and penetrate the ground 18 which is to be searched for location of a buried object 20. Preferably the mouth 17 of the tube 16 is held between one centimeter and 10 centimeters above the surface of the ground 18.

A pair of microphones M1 and M2 are held in vibration isolation mounts (not shown) each at a distance of approximately 2 centimeters to 50 centimeters from the tube and at approximately the same distance from the ground as the mouth 17 of the tube 16.

The microphones M1 and M2 are connected to a processing means such as a data 6000 waveform analyser 22.

Instead of providing a separate speaker 12, amplifier and waveform synthesiser 14 and waveform analyser 22, those components can be integrated into a single circuit or furtherstill the waveform analyser 22 could be replaced by a PC or other suitable computer (not shown).

Figure 3A:
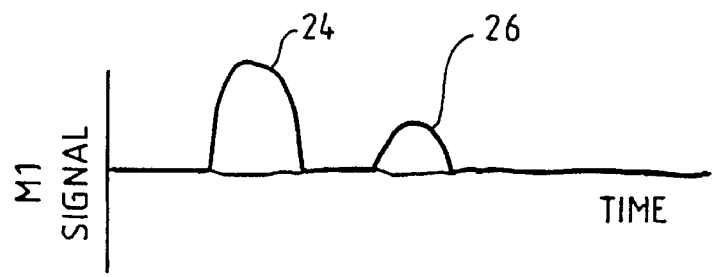
FIGS. 3A, 3B and 3C are graphs in idealised form illustrating operation of the preferred embodiments of the invention.
Figure 3B:
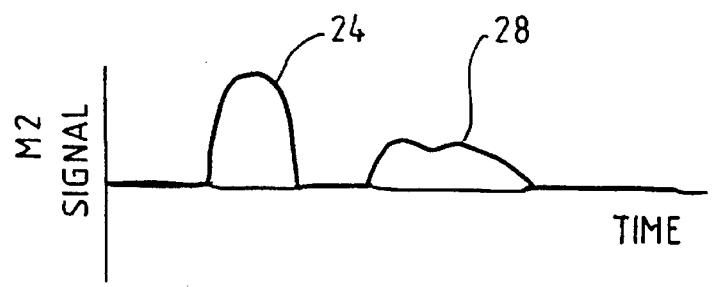
Figure 3C:
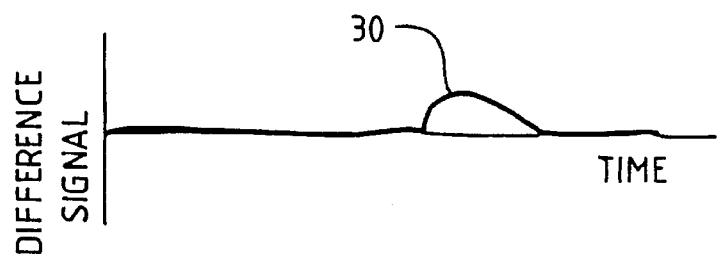

FIGS. 3A, 3B and 3C show idealised signals received from the microphones M1 and M2 and a difference signal which will be explained hereinafter.

The graph in FIG. 3A shows a signal from microphone M1 which is above ground in which no object is buried. The portion of the signal 24 represents the direct pulse from speaker 12 and the portion 26 represents the reflection from the ground 18.

The signal from microphone M2 has the same direct pulse characteristic 24, but a modified reflection characteristic from within the ground 18 due to the object 20. Reflection from the object 20 caused by the change of impedance in the ground in view of the object 20 modifies the signal 26 in FIG. 3A to the form 28 shown in FIG. 3B.

The signal detected by the microphone M1 which is over ground in which nothing is buried therefore provides a reference signal so that when the signal shown in FIG. 3B is subtracted from the signal shown in FIG. 3A the difference signal shown in FIG. 3C is provided which has a characteristic 30 indicative of the object 20. If no object is present in the ground, the signals received by the microphones M1 and M2 are substantially identical (subject to random surface noise) and therefore the idealised difference signal obtained from the microphones M1 and M2 will be effectively 0. The inclusion of the characteristic signal 30 in FIG. 3C indicative of the object 20 enables an indication that an object is beneath the microphone M2 to be given, thereby locating the object 20 in the ground.

The waveform analyser 22 in FIG. 1 which receives the signals shown in FIGS. 3A and 3B from the microphones M1 and M2 analyses the signals by subtracting one from the other to produce the difference signals shown in 3C to thereby provide an indication of the object 20.

Figure 4A:
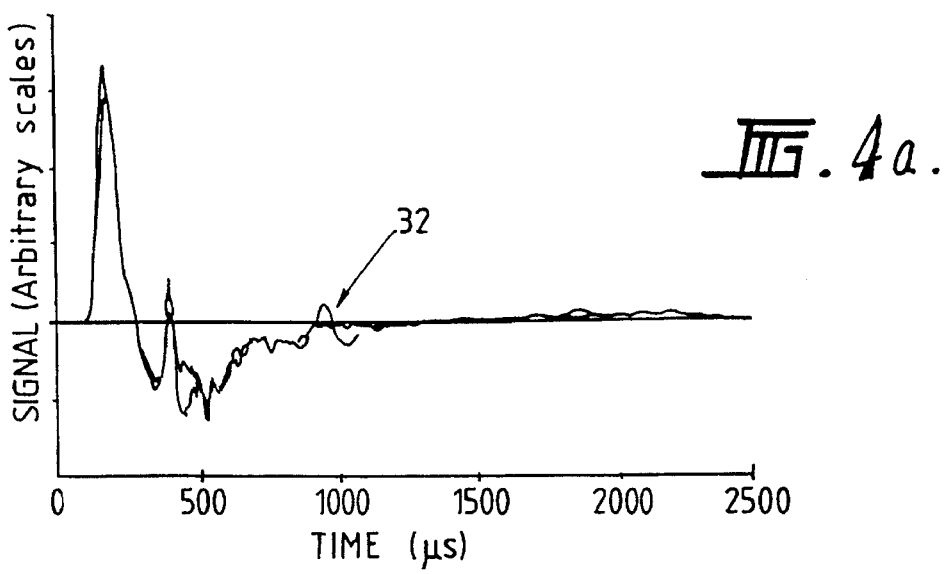
FIGS. 4A, 4B and 4C are graphs representing a real situation and illustrating correlation to compensate from random surface noise.
Figure 4B:
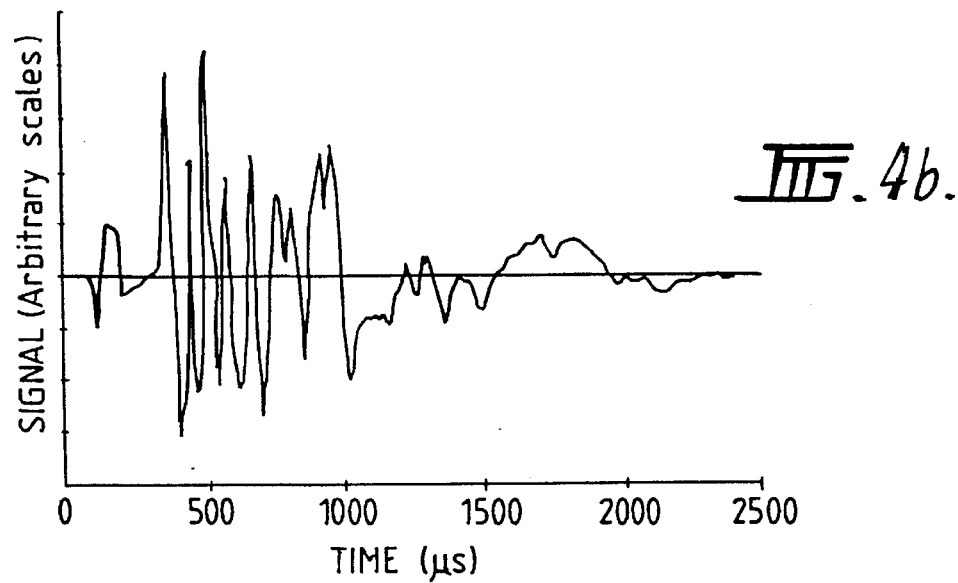
Figure 4C:
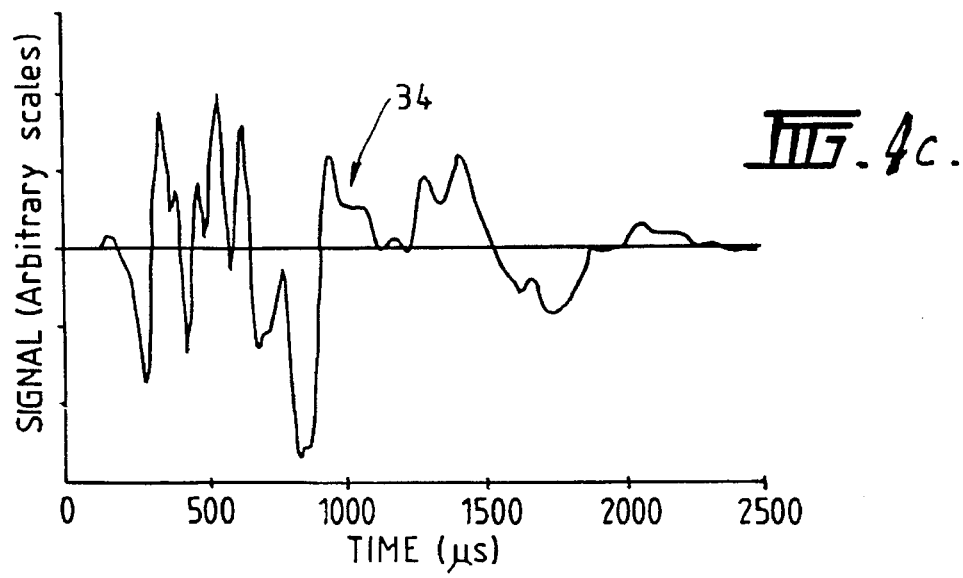

In actual measurements, the reflection from an uneven surface is sufficiently variable that the signals do not completely cancel as shown in FIGS. 3A to 3C leaving only a reflection from the object 20, and may partially overlap with the reflections from the object 20. A real situation is shown in FIGS. 4A, 4B and 4C. FIG. 4A shows the signals received from the microphones M1 and M2 with the reflection from the object 20 showing up as a small bump identified by reference numeral 32. The difference signal created by subtracting the signal from the microphone M1 from the signal from the microphone M2 is shown in FIG. 4B and is dominated by the residue arising from surface irregularities in the ground 18 preceding the required reflection. In order to compensate for the random surface noise, the difference signal is correlated with the signal produced by the speaker 12. The wanted reflection is a function of the original pulse waveform, but the random surface noise remaining after subtraction is only weakly related. Thus, use can be made of this fact by correlating the known direct pulse shape g(t) with the subtracted signal s(t) to obtain a modified signal x(t) where $$x(t) = \frac{\sum_{n=0}^{\infty} g(t)*s(t+n)}{[g(t)]^2}$$

This process enhances the required reflection as the output and is shown in FIG. 4C. The output shown in FIG. 4C has a large magnitude wherever a portion of the subtracted signal has the same waveform as the direct pulse. FIG. 4C shows after correlating in accordance with the above function, there is a significant enhancement of the reflection identified by reference 34 in FIG. 4C.

Figure 2:
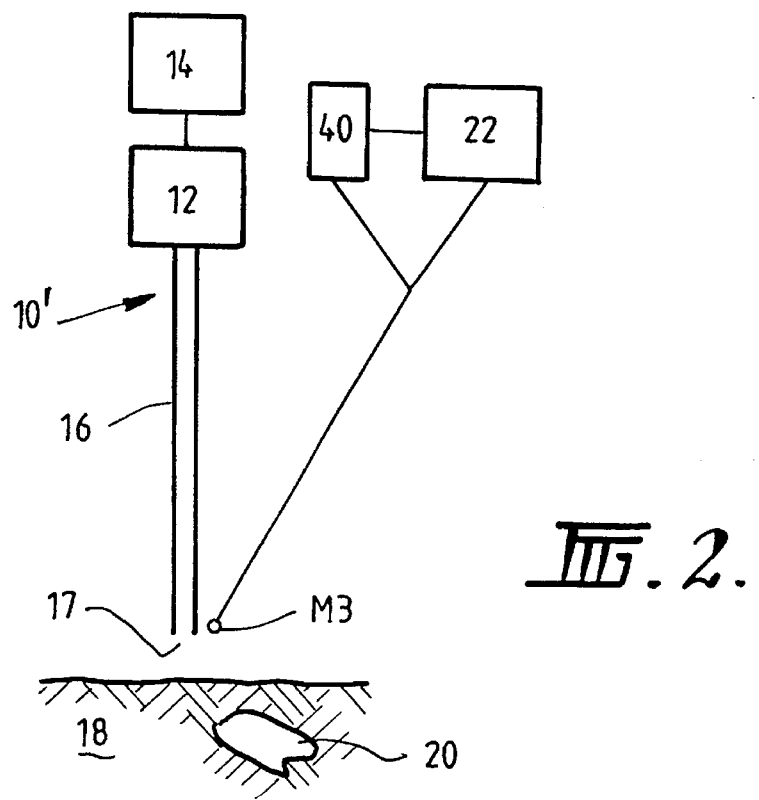
FIG. 2 is a schematic view showing a second embodiment of the invention.

FIG. 2 shows a second embodiment of the invention in which similar reference numerals represent the same features as those described with reference to FIG. 1. In this embodiment, a single microphone M3 is utilised which is arranged adjacent the mouth 17 of tube 16. Acoustic signals pass down the tube 16 from speaker 12 as in the earlier embodiment and penetrate the ground 18. As the device 10' shown in FIG. 2 is moved over the ground, the microphone M3 will detect reflections from the ground 18 where no object is buried and, of course, when the tube 16 is above the object 20 will detect reflections from the object 20. Reflections which are detected by the microphone M3 whilst the device 10' is away from the object 20 are stored in a storage such as a memory 40 which therefore contains data which forms the reference signal which is used for comparison to determine whether an object 20 has been located. The reference signal stored in the memory 40 can be updated from time to time as the detector is moved over similar terrain and a comparison can be made to determine that reference signals do not depart from one another by a significant degree to prevent false storage of a reference signal which may in fact be a reflection from an object 20. As the device 10' continues to be passed over the ground, the object 20 when located will produce a signal with the reflection characteristic 32 as shown in FIG. 4A. When this signal is compared with the signal stored in storage 40 in the manner described above, the correlated difference signals shown in 4C can be generated to thereby provide an indication of the object 20.

Thus, in the embodiment of FIG. 2 instead of providing a continuous pulsed reference signal by use of a second microphone, the reference signal is obtained earlier in time than location of the object 20 and stored in the memory for comparison with signals received by the microphone M3 to provide an indication of whether or not the object 20 has been located.

The preferred embodiment of the invention also includes isolation of part of the correlated difference signal shown in FIG. 4C within a window to thereby include only a portion of the trace where an object reflection may occur. Reflections from the surface of the ground will be received by the microphones M1 to M3 before reflection from the object 20 and therefore by time isolation within a window only the portions of the trace where the object reflection may occur can be considered. The position of the time window can be adjusted to suit the depths being examined. For a deeply buried object, there will be a greater time delay before the appropriate reflection arrives at the microphone M1 to M3 and so the appropriate time window will occur later. For example, in FIG. 4C a window could be defined commencing 620 microseconds along the correlated difference signal shown in FIG. 4C and lasting for a duration of 320 microseconds. By adjusting the position of the window, only certain depths below ground level can be analysed or alternatively, a number of different windows can be used to thereby locate an object at a random depth and thereby provide an indication of the depth of the object below ground level as well as the existence of the object itself.

Figure 5:
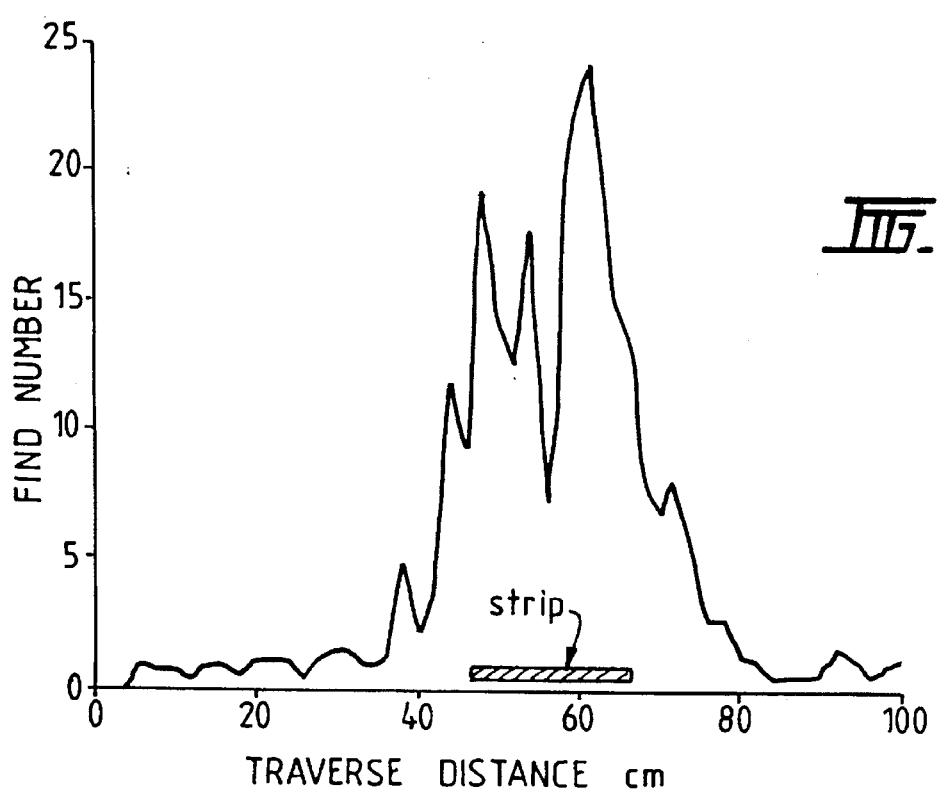
FIG. 5 is a graph illustrating an output which may be provided by the object detector illustrating location of an object and also illustrating time isolating with a window to provide an indication of depth of the object.

In order to assist in the identification of objects, an arbitrary value, such as a so called find number referred to in FIG. 5, can be determined and which can be associated with particular types of objects to thereby provide an indication of the nature of an object. FIG. 5 shows a graph of find number against distance the detector was moved across an object buried in the ground. In FIG. 5, the detector of FIG. 1 was progressively moved in 2 centimeter steps across a buried strip of material. The minimum at the middle of the strip occurs because the detector is directly above the strip and therefore both microphones M1 and M2 record essentially the same signal. The find number shown in the graph of FIG. 5 is generated by integrating the relevant part of the signal shown in FIG. 4C (that is, the portion 34 shown in FIG. 4C). By experimentation various find numbers can be associated to various different shaped objects to thereby provide not only an indication of the existence of an object below ground, but the shape the object may have. The find number can be generated by the processor 22 and can be displayed on an LED display (not shown) or the like.

Figure 6:
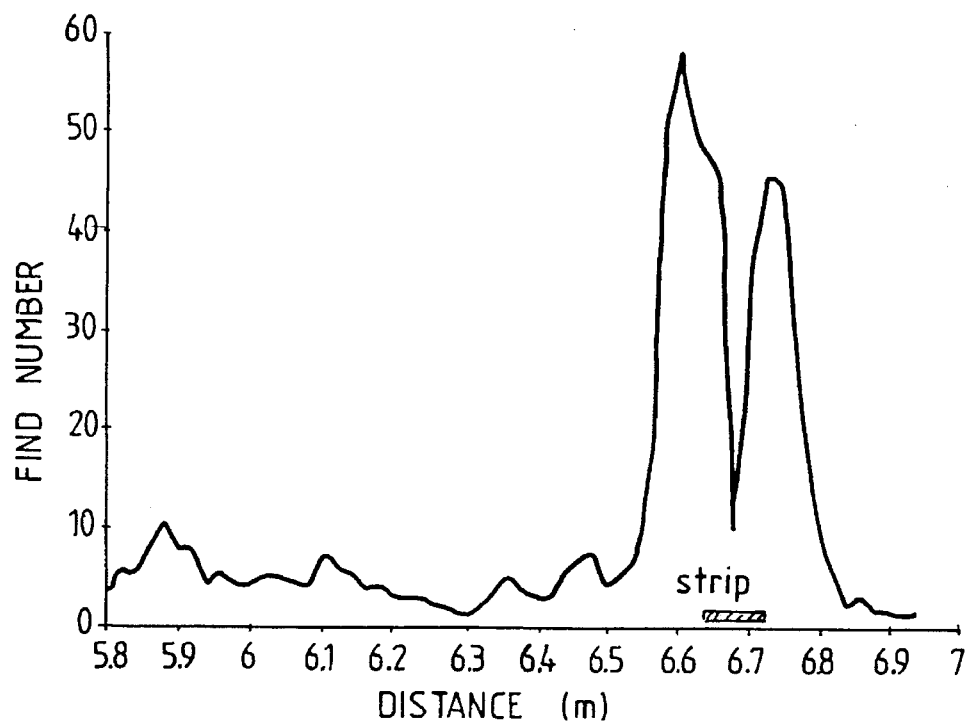
FIGS. 6, 7, 8 and 9 are graphs showing various types of objects and different outputs which can be obtained to thereby enable identification of objects.
Figure 7:
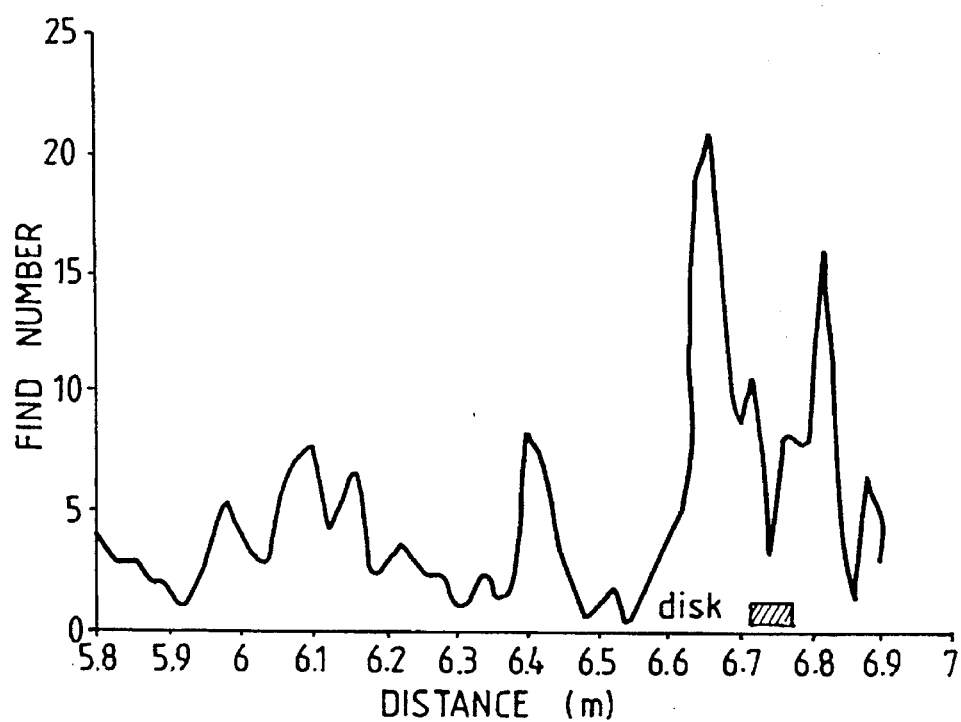
Figure 8:
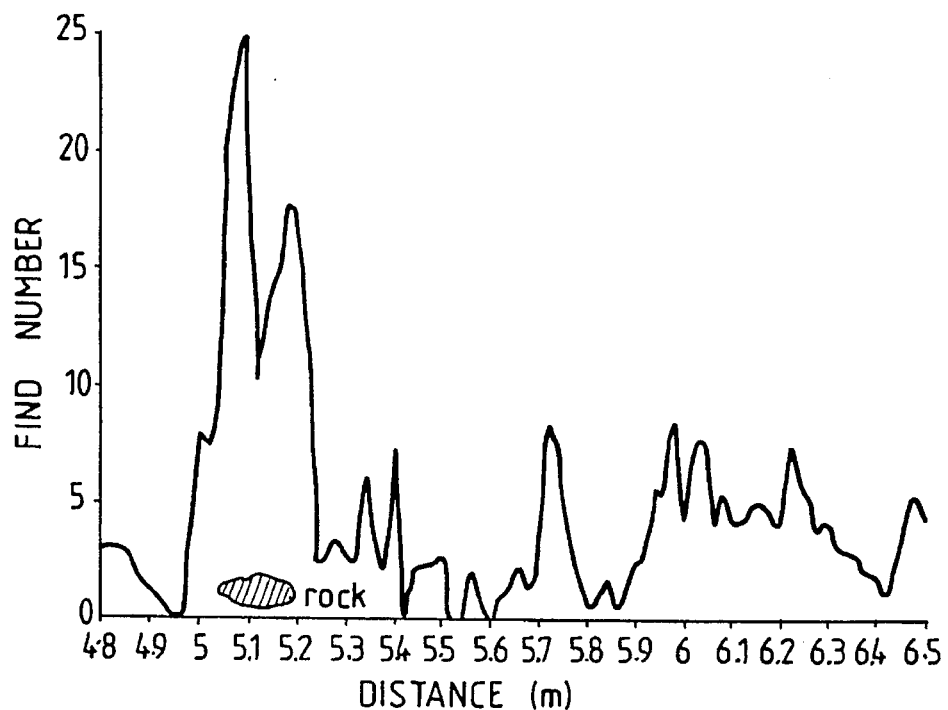
Figure 9:
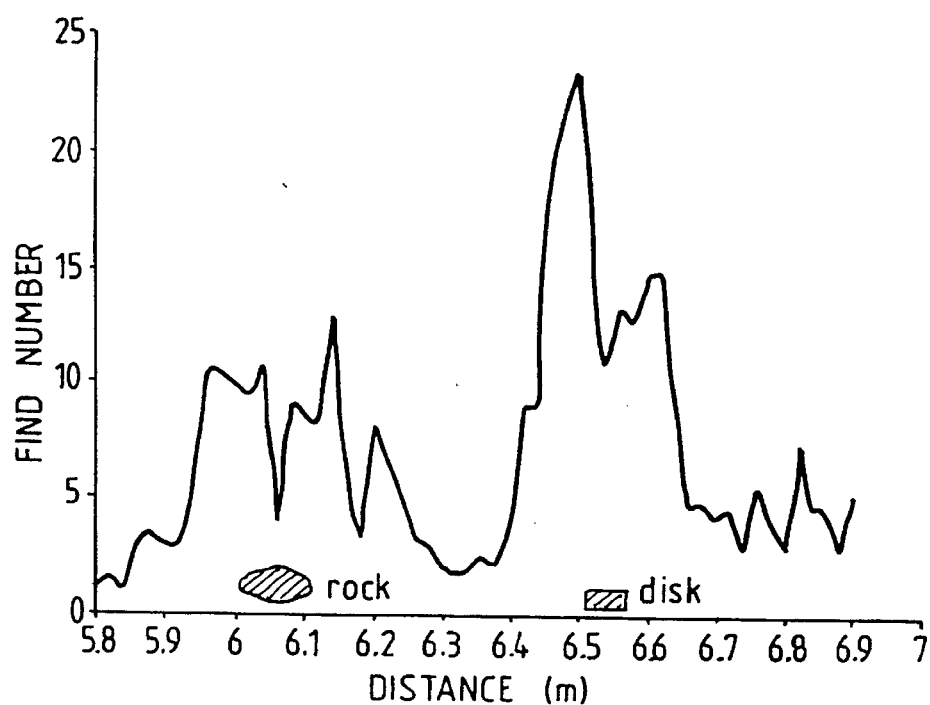

FIGS. 6 to 9 show graphs similar to FIG. 5 of various different shaped objects detailing the find number relating to those objects. FIG. 6 shows a 9 centimeter wide plastic strip, FIG. 7 a 6 centimeter diameter plastic disc and FIG. 8 a similar size but irregularly shaped rock all buried 5 centimeters under pebbles. FIG. 9 shows it is possible to distinguish between a rock and a disc buried approximately 50 centimeters apart.

Figure 10:
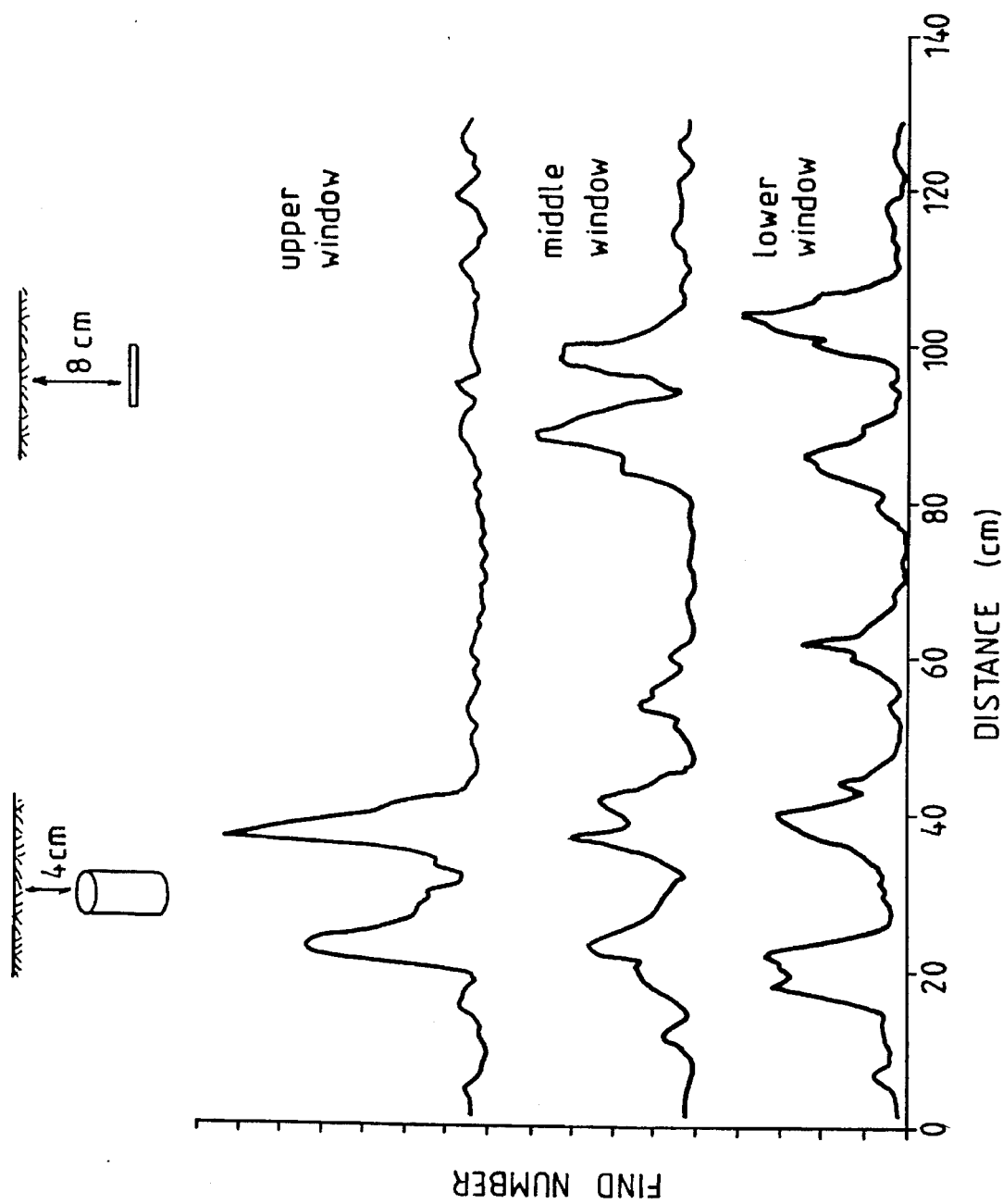
FIG. 10 is a graph illustrating time allocated windows used in the processing according to the preferred embodiment of the invention.

FIG. 10 shows the setting of a number of windows along the correlated difference signal to distinguish objects of different depths. If the speed of sound in the ground is known, then the time position of the windows can be set for particular depths. FIG. 10 shows this approach using three windows with the upper window looking in the region from 1 to 5 centimeters, the middle window in the region 5 to 9 centimeters, while the third window scanned 9 to 12 centimeter depths. Two plastic objects were buried in a pebble matrix—a cylinder (6 centimeters diameter, 10 centimeters long) was set vertically about 4 centimeters deep while a 5 centimeter flat strip was located 8 centimeters below the surface. The find patterns are shown in FIG. 10. While the upper window did not sense the more deeply buried strip, the lower windows still responded to an object closer to the surface. The reason for this will be two-fold. Firstly, there may well be a residue signal in the correlated difference extending beyond the setting of the upper window. Secondly, the microphone nearest the object will continue to receive a reflection from it, but which becomes progressively more delayed as the probe moves further away. Thus, a horizontal displacement is equivalent, in time, to the effect of a deeper buried object. This would account for the progressively wider signals produced in the lower windows.

In the preferred embodiments of the invention, the processor 22 may also include a frequency filter related to the known spectrum of the source for filtering the reflected signals and modification of the waveform which is used in the correlation to compensate for the approximate impedance of the ground.

Since modifications within the spirit and scope of the invention may readily be effected by persons skilled within the art, it is to be understood that this invention is not limited to the particular embodiment described by way of example hereinabove.

We claim:

1. An object detector for detecting objects buried in the ground, including
    a source for producing an acoustic signal comprised of short duration pulses and for directing the signal towards the ground so that the acoustic signal penetrates the ground;
    a sensor for detecting a reflected signal from the ground where no buried object is located to provide a reference signal and for detecting an object reflected signal from the object; and
    processing means for subtracting the object reflected signal from the reference signal or vise versa, during a predetermined time period, to thereby provide an indication of said object:
    wherein the processing means correlates a difference signal, which is the difference between the object reflected signal and the reference signal, with the acoustic signal to compensate for random surface noise to obtain a modified signal x(t)

$$x(t) = \frac{\sum_{n=0}^{\infty} g(t)*s(t+n)}{[g(t)]^2}$$

wherein g(t) is the shape of the acoustic signal, and s(t) is the reflected signal.

2. An object detector for detecting objects buried in the ground, including:
    a source for producing an acoustic signal and for directing the acoustic signal towards the ground so that the acoustic signal penetrates the ground;
    a single sensor for, when the object detector is passed over the ground, detecting a reflected signal from the ground other than where the object is buried to thereby provide a reference signal and for detecting a reflected signal from the object;
    a storage means for storing data relating to the reference signal; and
    processing means for subtracting the reflected signal from the data relating to the reference signal stored in the storage means, or vice versa to thereby provide an indication of said object:
    wherein the processing means correlates a difference signal, which is the difference between the object reflected signal and the reference signal, with the acoustic signal to compensate for random surface noise to obtain a modified signal x(t)

$$x(t) = \frac{\sum_{n=0}^{\infty} g(t)*s(t+n)}{[g(t)]^2}$$

wherein g(t) is the shape of the acoustic signal, and s(t) is the reflected signal.

* * * * *